(12) United States Patent
Fischer et al.

(10) Patent No.: US 9,765,046 B2
(45) Date of Patent: Sep. 19, 2017

(54) PROCESS FOR PREPARING PHTHALIC ANHYDRIDE

(71) Applicant: BASF SE, Ludwigshafen (DE)

(72) Inventors: Nico F. Fischer, Heidelberg (DE); Michael Krämer, Katzweiler (DE); Jürgen Zühlke, Speyer (DE); Hans-Martin Allmann, Neunkirchen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/900,663

(22) PCT Filed: Jun. 16, 2014

(86) PCT No.: PCT/IB2014/062255
§ 371 (c)(1),
(2) Date: Dec. 22, 2015

(87) PCT Pub. No.: WO2014/207603
PCT Pub. Date: Dec. 31, 2014

(65) Prior Publication Data
US 2016/0145226 A1    May 26, 2016

(30) Foreign Application Priority Data
Jun. 26, 2013 (EP) ..................... 13173693

(51) Int. Cl.
 *C07D 307/89*  (2006.01)
 *C07C 51/265* (2006.01)
 *C07C 51/31*  (2006.01)

(52) U.S. Cl.
 CPC .......... *C07D 307/89* (2013.01); *C07C 51/265* (2013.01); *C07C 51/313* (2013.01)

(58) Field of Classification Search
 CPC .................................................. C07D 307/89
 USPC ....................................................... 549/249
 See application file for complete search history.

(56) References Cited

U.S. PATENT DOCUMENTS

| | | | |
|---|---|---|---|
| 3,976,666 A | 8/1976 | Hoffmann et al. | |
| 4,411,818 A | 10/1983 | Reuter et al. | |
| 6,700,000 B1 | 3/2004 | Heidemann et al. | |
| 6,774,246 B2 | 8/2004 | Reuter et al. | |
| 7,151,184 B2 | 12/2006 | Storck et al. | |
| 7,592,294 B2 | 9/2009 | Storck et al. | |
| 7,985,705 B2 | 7/2011 | Storck et al. | |
| 9,029,289 B2 | 5/2015 | Kramer et al. | |
| 2005/0101803 A1 | 5/2005 | Dieterle et al. | |
| 2007/0135302 A1 | 6/2007 | Neto et al. | |
| 2014/0213801 A1 | 7/2014 | Altwasser et al. | |

FOREIGN PATENT DOCUMENTS

| | | |
|---|---|---|
| DE | 1958776 A1 | 6/1971 |
| DE | 2340047 A1 | 3/1975 |
| DE | 40 06 935 A1 | 9/1991 |
| DE | 10 2010006854 A1 | 8/2011 |
| EP | 061018 A1 | 9/1982 |
| EP | 1084115 A1 | 3/2001 |
| EP | 1670741 A1 | 6/2006 |
| GB | 1281631 A | 7/1972 |
| WO | WO-9961433 A1 | 12/1999 |
| WO | WO-0216299 A1 | 2/2002 |
| WO | WO-03070680 A1 | 8/2003 |
| WO | WO-2004103561 A1 | 12/2004 |
| WO | WO-2005/030388 A1 | 4/2005 |
| WO | WO-2005030692 A1 | 4/2005 |
| WO | WO-2005042459 A1 | 5/2005 |
| WO | WO-2011/061132 A1 | 5/2011 |
| WO | WO-2011/128814 A1 | 10/2011 |

OTHER PUBLICATIONS

International Search Report for PCT/IB2014/062255 mailed Feb. 26, 2015.
Bo et al., "Analysis on the Stability of Catalyst o—Xylene Oxidation to Phthalic Anhydride", Petrochemical Technology, vol. 5, pp. 421-423 (2004).
U.S. Appl. No. 14/900,698, Kramer et al.

*Primary Examiner* — Taofiq A Solola

(74) *Attorney, Agent, or Firm* — Drinker Biddle & Reath LLP

(57) ABSTRACT

The present invention relates to a process for preparing phthalic anhydride by gas phase oxidation of aromatic hydrocarbons, in which a gas stream comprising at least one aromatic hydrocarbon and molecular oxygen is passed continuously over a thermostatted catalyst and the supply of the at least one aromatic hydrocarbon to the catalyst is temporarily interrupted after putting the catalyst on stream.

13 Claims, No Drawings

PROCESS FOR PREPARING PHTHALIC ANHYDRIDE

CROSS-REFERENCE TO RELATED APPLICATIONS

This application is a national stage application (under 35 U.S.C. §371) of PCT/IB2014/062255, filed Jun. 16, 2014, which claims benefit of European Application No. 13173693.6, filed Jun. 26, 2013, both of which are incorporated herein by reference in their entirety.

The present invention relates to a process for preparing phthalic anhydride by gas phase oxidation of aromatic hydrocarbons, in which a gas stream comprising at least one aromatic hydrocarbon and molecular oxygen is passed continuously over a thermostatted catalyst and the supply of the at least one aromatic hydrocarbon to the catalyst is temporarily interrupted after putting the catalyst on stream.

A multitude of carboxylic acids and/or carboxylic anhydrides is prepared industrially by the catalytic gas phase oxidation of hydrocarbons such as benzene, the xylenes, naphthalene, toluene or durene in fixed bed reactors. In this way, it is possible to obtain, for example, benzoic acid, maleic anhydride, phthalic anhydride (PA), isophthalic acid, terephthalic acid or pyromellitic anhydride. For example, phthalic anhydride is prepared industrially by catalytic gas phase oxidation of o-xylene and/or naphthalene. The starting material is a mixture of a molecular oxygen-comprising gas, for example air, and the o-xylene and/or naphthalene to be oxidized. The mixture is passed through a multitude of tubes arranged within a reactor (shell-and-tube reactor), in which there is a bed of at least one catalyst. For temperature regulation and thermostatting, the tubes are surrounded by a heat carrier medium, for example a salt melt.

The catalytic gas phase oxidation of o-xylene and/or naphthalene to PA is common knowledge and is described, for example, in WO 2004/103561. Since the reaction is strongly exothermic, temperature maxima (called hotspots) develop within the reactor, which are typically within the temperature range from 400 to 500° C., especially within the temperature range from 410 to 460° C. Hotspot temperatures above 500° C. lead to a significant decrease in the achievable PA yield and in the catalyst service life. Excessively low hotspot temperatures, in contrast, lead to an excessively large content of underoxidation products in the phthalic anhydride (especially phthalide and naphthoquinone), which crucially impair the product quality. The hotspot temperature depends upon factors including the reactant loading of the gas stream, the level of the catalyst hourly space velocity, the aging state of the catalyst, the characteristic heat transfer conditions of the reactor (which depend upon factors including the reactor tube dimensions and the salt bath volume) and the temperature of the heat carrier medium.

Setting the temperature and keeping it constant is thus of great significance for the performance of the process, which is measured primarily by the PA yield obtained and by the purity thereof. High-quality PA (cf. DE 10 2010 006 854 A1, WO 2011/128814 A1) is notable for minimum contents both of underoxidation products (especially phthalide and naphthoquinone) and of unconverted o-xylene and naphthalene, since these substances can be separated from one another only with very great difficulty and adversely affect the color number of the finished pure PA.

The influence of startup and rundown operations on the stability of catalysts for the oxidation of o-xylene to PA in a model experiment has been studied and described by H. Bo et al. in Petrochemical Technology 2004, Vol. 5, pages 421 to 423.

There is a constant need for improved processes for gas phase oxidations which enable a maximum conversion at high selectivity and product purity.

It was an object of the present invention to provide a process for preparing phthalic anhydride by gas phase oxidation of aromatic hydrocarbons, which gives a product of maximum purity with high conversion and simultaneously high selectivity.

This object is achieved by a process for preparing phthalic anhydride by gas phase oxidation of aromatic hydrocarbons, in which a gas stream comprising at least one aromatic hydrocarbon and molecular oxygen is passed continuously over a thermostatted catalyst and the supply of the at least one aromatic hydrocarbon to the catalyst is temporarily interrupted after putting the catalyst on stream.

The invention thus provides a process for preparing phthalic anhydride by gas phase oxidation of aromatic hydrocarbons, in which a gas stream comprising at least one aromatic hydrocarbon and molecular oxygen is passed continuously over a thermostatted catalyst, which comprises interrupting the supply of the at least one aromatic hydrocarbon to the catalyst for a period after putting the catalyst on stream and resuming the supply of the at least one aromatic hydrocarbon to the catalyst at the end of the period.

Useful catalysts for these oxidation reactions have been found to be what are called coated catalysts, in which the catalytically active material has been applied in the form of a shell on an inert support material such as steatite. The catalytically active constituents used in the catalytically active material of these coated catalysts are generally titanium dioxide and vanadium pentoxide. In addition, small amounts of a multitude of other oxidic compounds which influence the activity and selectivity of the catalyst as promoters may be present in the catalytically active material.

The inert support materials used may be virtually all prior art support materials, as used advantageously in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The catalyst supports can be used, for example, in the form of spheres, rings, tablets, spirals, tubes, extrudates or chippings. The dimensions of these catalyst supports correspond to those of catalyst supports used customarily for production of coated catalysts for the gas phase reactions of aromatic hydrocarbons. Preference is given to using steatite in the form of spheres having a diameter of 3 to 6 mm or of rings having an external diameter of 5 to 9 mm and a length of 3 to 8 mm and a wall thickness of 1 to 2 mm.

Catalysts suitable for the catalytic gas phase oxidation of o-xylene and/or naphthalene to PA comprise a catalytically active material which comprises at least vanadium oxide and titanium dioxide and can be applied to the support material in one or more shells. Different shells may differ in their composition.

Preferably, the catalytically active material, based on the total amount of the catalytically active material, comprises 1 to 40% by weight of vanadium oxide, calculated as $V_2O_5$, and 60 to 99% by weight of titanium dioxide, calculated as $TiO_2$. In preferred embodiments, the catalytically active material may additionally comprise up to 1% by weight of a cesium compound, calculated as Cs, up to 1% by weight of a phosphorus compound, calculated as P, and up to 10% by weight of antimony oxide, calculated as $Sb_2O_3$. All figures for the composition of the catalytically active material are based on the calcined state thereof, for example after calcination of the catalyst at 450° C. for one hour.

Typically, titanium dioxide in the anatase modification is used for catalytically active material. The titanium dioxide preferably has a BET surface area of 15 to 60 $m^2/g$, especially 15 to 45 $m^2/g$, more preferably 13 to 28 $m^2/g$. The titanium dioxide used may consist of a single titanium dioxide or a mixture of titanium dioxides. In the latter case, the value for the BET surface area is determined as the weighted mean of the contributions of the individual titanium dioxides. The titanium dioxide used consists, for example, advantageously of a mixture of a $TiO_2$ having a BET surface area of 5 to 15 $m^2/g$ and a $TiO_2$ having a BET surface area of 15 to 50 $m^2/g$.

Suitable vanadium sources are particularly vanadium pentoxide or ammonium metavanadate. Suitable antimony sources are various antimony oxides, especially antimony trioxide, Vanadium and antimony may additionally also be used in the form of a vanadium antimonate compound (WO 2011/061132). The vanadium antimonate incorporated in the active material of at least one layer can be prepared by reaction of any desired vanadium compounds and antimony compounds. Preference is given to the direct reaction of the oxides to give a mixed oxide or vanadium antimonate. The vanadium antimonate may have different molar ratios of vanadium to antimony, and may optionally also comprise further vanadium compounds or antimony compounds and be used in a mixture with further vanadium compounds or antimony compounds.

Useful phosphorus sources include especially phosphoric acid, phosphorous acid, hypophosphorous acid, ammonium phosphate or phosphoric esters, and in particular ammonium dihydrogenphosphate. Useful sources of cesium include the oxide or hydroxide or the salts which can be converted thermally to the oxide, such as carboxylates, especially the acetate, malonate or oxalate, carbonate, hydrogencarbonate, sulfate or nitrate.

As well as the optional additions of cesium and phosphorus, small amounts of a multitude of other oxidic compounds which influence the activity and selectivity of the catalyst as promoters, for example by lowering or increasing the activity thereof, may be present in the catalytically active material. Examples of such promoters include the alkali metals, more particularly (excluding cesium, which has been mentioned) lithium, potassium and rubidium, which are usually used in the form of their oxides or hydroxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide.

In addition, among the promoters mentioned, useful additives preferably also include the oxides of niobium and tungsten in amounts of 0.01 to 0.50% by weight, based on the catalytically active material.

The shell(s) of the coated catalyst are appropriately applied by spray application of a suspension of $TiO_2$ and $V_2O_5$, which optionally comprises sources of the abovementioned promoter elements, to the fluidized support (EP 1670741, WO 2005/030388). Before the coating, the suspension is preferably stirred for a sufficiently long period, for example 2 to 30 hours, especially 12 to 25 hours, to break up agglomerates of the suspended solids and to obtain a homogeneous suspension. The suspension typically has a solids content of 20 to 50% by weight. The suspension medium is generally aqueous, for example water itself or an aqueous mixture with a water-miscible organic solvent such as methanol, ethanol, isopropanol, formamide and the like.

In general, organic binders are added to the suspension, preferably copolymers, advantageously in the form of an aqueous dispersion, of acrylic acid/maleic acid, vinyl acetate/vinyl laurate, vinyl acetate/acrylate, styrene/acrylate and vinyl acetate/ethylene. The binders are commercially available as aqueous dispersions having a solids content of, for example, 35 to 65% by weight. The amount of such binder dispersions used is generally 2 to 45% by weight, preferably 5 to 35% by weight, more preferably 7 to 20% by weight, based on the weight of the suspension.

The support is fluidized in, for example, a fluidized bed apparatus in an ascending gas stream, especially air. The apparatuses usually consist of a conical or spherical vessel in which the fluidizing gas is introduced from the bottom or from the top through an immersed tube. The suspension is sprayed into the fluidized bed via nozzles from the top, at the side or from below. It is advantageous to use a riser tube arranged centrally or concentrically around the immersed tube. Within the riser tube, there is a higher gas velocity which transports the support particles upward. Within the outer ring, the gas velocity is only slightly above the fluidization velocity. Thus, the particles are moved vertically in a circular manner. A suitable fluidized bed apparatus is described, for example, in DE-A 4006935.

In the coating of the catalyst support with the catalytically active material, coating temperatures of 20 to 500° C. are generally employed, and the coating can be effected under atmospheric pressure or under reduced pressure. In general, the coating is effected at 0° C. to 200° C., preferably at 20 to 150° C., especially at 60 to 120° C.

The shell thickness of the catalytically active material is generally 0.02 to 0.2 mm, preferably 0.05 to 0.15 mm. The active material content in the catalyst is typically 5 to 25% by weight, usually 7 to 15% by weight.

As a result of thermal treatment of the precatalyst thus obtained at temperatures above 200 to 500° C., the binder escapes from the shell applied through thermal decomposition and/or combustion. Preference is given to effecting the thermal treatment in situ in the gas phase oxidation reactor.

It has been found to be particularly advantageous when a catalyst bed composed of various catalysts which differ in terms of their catalytic activity and/or chemical composition of the active material thereof, and which are introduced successively as layers in different zones of the reactor, is used. Preferably, when two reaction zones are employed, a catalyst used in the first reaction zone, i.e. that toward the inlet of the gas stream, is one which has a somewhat lower catalytic activity compared to the catalyst present in the second reaction zone, i.e. that toward the outlet of the gas stream. In general, the reaction is controlled through the temperature setting such that the majority of the aromatic hydrocarbons present in the gas stream is converted at maximum yield in the first zone. Preference is given to using three- to five-zone catalyst systems, especially three- and four-zone catalyst systems. A three-zone catalyst system for o-xylene oxidation to PA is described, for example, in EP 1084115.

Instead of mutually delimited zones of different catalysts, it is also possible to bring about a quasi-continuous transition of the zones and hence a quasi-homogeneous change in the active material composition or in the content thereof by inserting a zone with a mixture of the successive catalysts at the transition from one zone to the next zone.

The bed length of the first catalyst zone (CZ1) is preferably in the range from 10 to 50%, more preferably in the range from 15 to 30%, of the total catalyst fill height in the reactor. Typical reactors have a fill height of 250 cm to 400 cm. The catalyst zones may optionally also be distributed over several reactors.

In the process according to the invention, a gas stream comprising at least one aromatic hydrocarbon and molecular oxygen is passed continuously over such a thermostatted catalyst. The molecular oxygen is typically removed from air. The aromatic hydrocarbons used are preferably the xylenes or naphthalene and mixtures thereof, more preferably o-xylene or naphthalene and mixtures thereof. The catalytic gas phase oxidation of o-xylene and/or naphthalene to PA is frequently performed in a shell-and-tube reactor wherein the catalyst is present in the form of a bed in the tubes thereof. A gas stream comprising at least one aromatic hydrocarbon and molecular oxygen is passed through this catalyst bed at temperatures of generally 300 to 450° C., preferably 320 to 420° C. and more preferably 340 to 400° C., and at a gauge pressure of generally 0.1 to 2.5 bar, preferably 0.3 to 1.5 bar, and with a space velocity of generally 750 to 5000 $h^{-1}$, preferably 2000 to 5000 $h^{-1}$. The gas stream (reactant gas) supplied to the catalyst is generally produced by mixing a gas which comprises molecular oxygen and which may comprise, apart from oxygen, also suitable reaction moderators and/or diluents, such as steam, carbon dioxide and/or nitrogen, with the o-xylene and/or naphthalene to be oxidized. The gas stream comprises generally 1 to 100 mol %, preferably 2 to 50 mol % and more preferably 10 to 30 mol % of oxygen. In general, this gas stream is loaded with 5 to 140 g/m$^3$ (STP), preferably 60 to 120 g/m$^3$ (STP) and more preferably 80 to 120 g/m$^3$ (STP) of o-xylene and/or naphthalene. Before entering into the reactor, the gas stream is preheated to temperatures of 150 to 350° C.

To control the maximum temperatures which occur in the reactor during the reaction, the catalyst in the reactor is thermostatted, for instance by surrounding the reactor tubes with a heat carrier medium, for example a salt bath. In the case of use of a multizone catalyst, it is also possible for several separate salt bath circuits to be used, with which the temperatures of the individual zones can be controlled separately and optionally differently.

The service life of such catalysts is generally about 4 to 5 years. Because of the high initial activity thereof, a new catalyst has to be put on stream quite cautiously. Therefore, a relatively low loading of the gas stream with aromatic hydrocarbon is usually used at the start, and this is gradually increased over several months up to the desired target value of about 80 to 120 g/m$^3$ (STP).

In the context of this invention, a catalyst is considered to have been put on stream as soon as it has been contacted at least once at a reaction temperature of at least 300° C. with a gas stream comprising at least one aromatic hydrocarbon and molecular oxygen.

In one embodiment of the invention, the supply of the at least one aromatic hydrocarbon to the catalyst is interrupted for a period after the catalyst has been put on stream. This can be done, for example, by no longer adding any aromatic hydrocarbon to the gas stream passed over the catalyst. In that case, a hydrocarbon-free gas stream, the composition of which may vary, is passed over the catalyst during the inventive period. For example, air or inert gases such as nitrogen or noble gases (e.g. argon) or mixtures thereof with air can be passed over the catalyst during the period. The oxygen content of the gas stream can also be increased and may, for example, be up to 50% by volume.

In a further embodiment of the invention, the gas stream passed over the catalyst is shut down entirely. This gas stream may be interrupted directly or lowered gradually over a certain time period until full interruption is achieved. The supply of the aromatic hydrocarbon to the gas stream is first advantageously interrupted, and the reactor is purged with a hydrocarbon-free gas stream as described above until no further hydrocarbon is present in the reactor. Subsequently, the gas supply to the reactor is shut down entirely.

In any case, the catalyst is kept at its reaction temperature of at least 300° C. during the inventive period, for example by keeping the salt bath temperature constant.

The length of the inventive period over which no aromatic hydrocarbon is supplied to the catalyst after it has been put on stream can be varied very significantly and may be between a few minutes and up to one year. In a preferred embodiment of the invention, the length of this period is in the range of 30 minutes to 200 days, in a particularly preferred embodiment in the range of 1 hour to 120 days, in a very particularly preferred embodiment in the range of 2 hours to 60 days.

The inventive interruption of the supply of the aromatic hydrocarbon to the catalyst can be effected at any time after the catalyst has been put on stream. In order to obtain the improvement in the product quality achievable by the process according to the invention at once, very early performance of the process is advantageous. The process can also be performed during the startup phase, which generally lasts several months, i.e. before the desired maximum loading of the reactant gas with aromatic hydrocarbon has been attained. At the end of the period over which no aromatic hydrocarbon is supplied to the catalyst after it has been put on stream in accordance with the invention, the gas stream is optionally turned on again and charged again with at least one aromatic hydrocarbon. In one embodiment of the invention, the same settings are selected for the temperature of the heat carrier medium, the gas flow rate and the loading of the gas stream with aromatic hydrocarbon which were used before the interruption of the supply of the aromatic hydrocarbon to the catalyst.

In a preferred embodiment of the invention, at the end of the inventive period, the temperature of the heat carrier medium is set to a higher value than before the interruption of the supply of the aromatic hydrocarbon to the catalyst. In a particularly preferred embodiment of the invention, the temperature of the heat carrier medium is set 1 to 5° C. higher than before the interruption of the supply of the aromatic hydrocarbon to the catalyst, most preferably 1 to 3° C. higher.

In a further preferred embodiment of the invention, at the end of the inventive period, the gas flow rate is set to a lower value than before the interruption of the supply of the aromatic hydrocarbon to the catalyst. In a particularly preferred embodiment of the invention, the gas flow rate is set to a value 5 to 15% lower than before the interruption of the supply of the aromatic hydrocarbon to the catalyst.

In a further preferred embodiment of the invention, at the end of the inventive period, the loading of the gas stream with aromatic hydrocarbon is set to a lower value than before the interruption of the supply of the aromatic hydrocarbon to the catalyst. In a particularly preferred embodiment of the invention, the loading of the gas stream with aromatic hydrocarbon is set to a value 5 to 30% lower than before the interruption of the supply of the aromatic hydrocarbon to the catalyst.

If, after restarting the supply of the aromatic hydrocarbon to the catalyst, settings which differ from the settings that were used before the interruption of the supply of the aromatic hydrocarbon to the catalyst are selected for the temperature of the heat carrier medium, the gas flow rate and the loading of the gas stream with aromatic hydrocarbon, the settings can generally be restored within a few days back to the values which have been used before the interruption of the supply of the aromatic hydrocarbon to the catalyst.

The process according to the invention achieves a distinct improvement in the product quality, expressed in reduced contents of unconverted aromatic hydrocarbon and also of underoxidation products such as phthalide or naphthoquinone in the PA obtained.

The process according to the invention can also be used to improve the product quality in catalytic gas phase oxidations for preparation of other carboxylic acids and/or carboxylic anhydrides.

The invention further provides for the use of the above-described process for improving product quality in phthalic anhydride preparation.

The examples which follow illustrate the invention without restricting it.

EXAMPLES

Example 1 (Inventive)

Catalyst Zone 1 (CZ1) (Vanadium Antimonate as V and Sb Source):
Preparation of the Vanadium Antimonate:
2284.1 g of vanadium pentoxide and 1462 g of antimony trioxide (Antraco ACC-BS, approx. 4% valentinite and 96% senarmontite; $Sb_2O_3 \geq 99.8\%$ by weight: As$\leq$800 ppm by weight, Pb$\leq$800 ppm by weight, Fe$\leq$30 ppm by weight, mean particle size=1.4 μm) were suspended in 5.6 of demineralized water and the suspension was stirred under reflux for 15 hours. Thereafter, the suspension was cooled to 80° C. and dried by means of spray drying. The inlet temperature was 340° C., the exit temperature 110° C. The spray powder thus obtained had a BET surface area of 89 $m^2/g$ and had a vanadium content of 32% by weight and an antimony content of 30% by weight. The product had the following crystalline constituents: valentinite (ICPDS: 11-0689): approx. 3%; senarmontite (ICPDS: 43-1071): approx. 2%; vanadium antimonate (ICPDS: 81-1219): approx. 95%. The mean crystal size of the vanadium antimonate was approx. 9 nm, Suspension mixing and coating:

2 kg of steatite rings (magnesium silicate) having dimensions of 7 mm×7 mm×4 mm were coated in a fluidized bed apparatus with 752 g of a suspension of 4.4 g of cesium carbonate, 413.3 g of titanium dioxide (Fuji TA 100 CT; anatase, BET surface area 27 $m^2/g$), 222.5 g of titanium dioxide (Fuji TA 100; anatase, BET surface area 7 $m^2/g$), 86.9 g of vanadium antimonate (as prepared above), 1870.1 g of demineralized water and 76.7 g of organic binder (copolymer of vinyl acetate and vinyl laurate in the form of a 50% by weight aqueous dispersion).

After calcination of the catalyst at 450° C. for one hour, the active material applied to the steatite rings was 8.4%. The analyzed composition of the active material consisted of 7.1% $V_2O_5$, 4.5% $Sb_2O_3$, 0.50% Cs, remainder $TiO_2$.

Catalyst Zone 2 (CZ2) (Vanadium Pentoxide and Antimony Trioxide, Respectively, as V and Sb Sources):
2 kg of steatite rings (magnesium silicate) having dimensions of 7 mm×7 mm n4 mm were coated in a fluidized bed apparatus with 920 g of a suspension of 3.0 g of cesium carbonate, 446.9 g of titanium dioxide (Fuji TA 100 C; anatase, BET surface area 20 $m^2/g$), 133.5 g of titanium dioxide (Fuji TA 100; anatase, BET surface area 7 $m^2/g$), 45.4 g of vanadium pentoxide, 11.6 g of antimony trioxide, 1660.1 g of demineralized water and 104.5 g of organic binder (copolymer of vinyl acetate and vinyl laurate in the form of a 50% by weight aqueous dispersion).

After calcination of the catalyst at 450° C. for one hour, the active material applied to the steatite rings was 10.0%. The analyzed composition of the active material consisted of 7.1% $V_2O_5$, 1.8% $Sb_2O_3$, 0.38% Co. remainder $TiO_2$.

Catalyst Zone 3 (CZ3) (Vanadium Pentoxide and Antimony Trioxide, Respectively, as V and Sb Sources):
2 kg of steatite rings (magnesium silicate) having dimensions of 7 mm×7 mm×4 mm were coated in a fluidized bed apparatus with 750 g of a suspension of 2.33 g of cesium carbonate, 468.7 g of titanium dioxide (Fuji TA 100 C; anatase, BET surface area 20 $m^2/g$), 76.3 g of titanium dioxide (Fuji TA 100; anatase, BET surface area 7 $m^2/g$), 48.7 g of vanadium pentoxide, 16.7 g of antimony trioxide, 1588.0 g of demineralized water and 85.2 g of organic binder (copolymer of vinyl acetate and vinyl laurate in the form of a 50% by weight aqueous dispersion).

After calcination of the catalyst at 450° C. for one hour, the active material applied to the steatite rings was 8.4%. The analyzed composition of the active material consisted of 7.95% $V_2O_5$, 2.7% $Sb_2O_3$, 0.31% Cs, remainder $TiO_2$.

Catalyst Zone 4 (CZ4) (Vanadium Pentoxide and Antimony Trioxide, Respectively, as V and Sb Sources):
2 kg of steatite rings (magnesium silicate) having dimensions of 7 mm×7 mm×4 mm were coated in a fluidized bed apparatus with 760 g of a suspension of 1.7 g of cesium carbonate, 370.1 g of titanium dioxide (Fuji TA 100 CT; anatase, BET surface area 27 $m^2/g$), 158.6 g of titanium dioxide (Fuji TA 100; anatase, BET surface area 7 $m^2/g$), 67.3 g of vanadium pentoxide, 14.8 g of antimony trioxide, 1587.9 g of demineralized water and 86.3 g of organic binder (copolymer of vinyl acetate and vinyl laurate in the form of a 50% by weight aqueous dispersion).

After calcination of the catalyst at 450° C. for one hour, the active material applied to the steatite rings was 8.7%. The analyzed composition of the active material consisted of 11% $V_2O_5$, 2.4% $Sb_2O_3$, 0.22% Co. remainder $TiO_2$.

Catalyst Zone 5 (CZ5) (Vanadium Pentoxide and Antimony Trioxide, Respectively, as V and Sb Sources):
2 kg of steatite rings (magnesium silicate) having dimensions of 7 mm×7 mm×4 mm were coated in a fluidized bed apparatus with 850 g of a suspension of 389.8 g of titanium dioxide (Fuji TA 100 CT; anatase, BET surface area 27 $m^2/g$), 97.5 g of titanium dioxide (Fuji TA 100; anatase, BET surface area 7 $m^2/g$), 122.4 g of vanadium pentoxide, 1587.9 g of demineralized water and 96.5 g of organic binder (copolymer of vinyl acetate and vinyl laurate in the form of a 50% by weight aqueous dispersion).

After calcination of the catalyst at 450° C. for one hour, the active material applied to the steatite rings was 9.1%. The analyzed composition of the active material consisted of 20% $V_2O_5$, 0.38% P, remainder $TiO_2$.

The catalytic oxidation of o-xylene to phthalic anhydride was performed in a salt bath-cooled tubular reactor having an internal tubular diameter of 25 mm. From reactor inlet to reactor outlet, 80 cm of CZ1, 60 cm of CZ2, 70 cm of CZ3, 50 cm of CZ4 and 60 cm of CZ5 were introduced into an iron tube of length 3.5 m with internal width 25 mm. For temperature regulation, the iron tube was surrounded by a salt melt; a 4 mm external diameter thermowell with installed tensile element served for catalyst temperature measurement.

4.0 m³ (STP) of air per hour flowed through the tube from the top downward with loadings of 99 to 99.4% by weight o-xylene of 30 to 100 g/m³ (STP). After a run time of 172 days, at a salt bath temperature of 346° C., an air flow rate of 4 m³ (STP)/h and an o-xylene loading of 100 g/m³ (STP), the supply of the reactant gas to the catalyst was interrupted for 6 hours and replaced by nitrogen (reactor inlet pressure=260 mbar). After the 6 hours, the catalyst was charged again under conditions identical to before the shutdown with o-xylene-laden air, i.e. a salt bath temperature of 346° C., an air flow rate of 4 m³ (STP)/h and an o-xylene loading of 100 g/m³ (STP). After four further days, the product gas composition was analyzed (see Table 1).

TABLE 1

|  | Before the shutdown | After the shutdown |
|---|---|---|
| Days since shutdown | 0 | 4 |
| Air rate [m³ (STP)/h] | 4.0 | 4.0 |
| Loading [$g_{o-x}$/m³ (STP)] | 100 | 100 |
| Salt bath temperature [° C.] | 346 | 346 |
| o-Xylene [% by wt.] | 0.071 | 0.070 |
| Phthalide [% by wt.] | 0.119 | 0.100 |

It has been found that, under identical conditions, the product quality after the interruption of the supply of the aromatic hydrocarbon to the catalyst was improved, recognizable by the reduction in the content of phthalide, an underoxidation product, at constant o-xylene concentration in the product.

Example 2 (Inventive)

4.0 m³ (STP) of air per hour flowed through a tube which corresponds to that described in example 1 and which has also been filled with the same catalyst bed as described in example 1 from the top downward with loadings of 99 to 99.4% by weight o-xylene of 30 to 100 g/m³ (STP). After a run time of 249 days, at a salt bath temperature of 351° C., an air flow rate of 4 m³ (STP)/h and an o-xylene loading of 100 g/m³ (STP), the supply of the reactant gas to the catalyst was interrupted for 52 days and replaced by nitrogen (reactor inlet pressure=260 mbar). The catalyst was subsequently started up again at an elevated salt bath temperature and a reduced o-xylene loading. Within two weeks, the settings as before the shutdown were attained and the product gas composition was analyzed (see Table 2).

TABLE 2

|  | Before the shutdown | Restart | After the shutdown |
|---|---|---|---|
| Days since shutdown | 0 | 52 | 66 |
| Air rate [m³ (STP)/h] | 4.0 | 4.0 | 4.0 |
| Loading [$g_{o-x}$/m³ (STP)] | 100 | 70 | 100 |
| Salt bath temperature [° C.] | 348 | 352 | 347.7 |
| o-Xylene [% by wt.] | 0.021 |  | 0.012 |
| Phthalide [% by wt.] | 0.054 |  | 0.032 |

Example 3 (Inventive)

The catalytic oxidation of o-xylene to phthalic anhydride was performed in a salt bath-cooled tubular reactor having an internal tubular diameter of 25 mm. From reactor inlet to reactor outlet, 90 cm of CZ1, 60 cm of CZ2, 70 cm of CZ3, 50 cm of CZ4 and 60 cm of CZ5 were introduced into an iron tube of length 3.5 m with internal width 25 mm. For temperature regulation, the iron tube was surrounded by a salt melt; a 4 mm external diameter thermowell with installed tensile element served for catalyst temperature measurement.

4.0 m³ (STP) of air per hour flowed through the tube from the top downward with loadings of 99 to 99.4% by weight o-xylene of 30 to 100 g/m³ (STP). After a run time of 50 days, at a salt bath temperature of 360° C., an air flow rate of 4 m³ (STP)/h and an o-xylene loading of 83 g/m³ (STP), the supply of the reactant gas to the catalyst was interrupted. The reactor was purged with air for about 2 minutes and then the gas supply was stopped entirely for 3 days. The catalyst was subsequently started up again at an elevated salt bath temperature, a reduced o-xylene loading and a reduced air flow rate. Within 7 days, the settings as before the shutdown were attained and the by-products in the product gas composition were analyzed (see Table 3).

TABLE 3

|  | Before the shutdown | Restart | After the shutdown |
|---|---|---|---|
| Days since shutdown | 0 | 3 | 10 |
| Air rate [m³ (STP)/h] | 4.0 | 3.8 | 4.0 |
| Loading [$g_{o-x}$/m³ (STP)] | 83 | 67 | 83 |
| Salt bath temperature [° C.] | 360 | 363 | 360 |
| o-Xylene [% by wt.] | 0.011 |  | 0.009 |
| Phthalide [% by wt.] | 0.025 |  | 0.019 |

Example 4 (Inventive)

4.0 m³ (STP) of air per hour with loadings of 99 to 99.4% by weight o-xylene of 30 to 100 g/m³ (STP) flowed from the top downward through a tube which corresponds to that described in example 3 and which has also been filled with the same catalyst bed as described in example 3. After a run time of 12 days, at a salt bath temperature of 367° C., an air flow rate of 4 m³ (STP)/h and an o-xylene loading of 58 g/m³ (STP), the supply of the reactant gas to the catalyst was interrupted. The reactor was purged with air for about 2 minutes and then the gas supply was stopped entirely for 12 hours. The catalyst was subsequently started up again at an elevated salt bath temperature, an equal o-xylene loading and a reduced air flow rate. Within 8 days, the settings as before the shutdown were attained and the by-products in the product gas composition were analyzed (see Table 4).

TABLE 4

|  | Before the shutdown | Restart | After the shutdown |
|---|---|---|---|
| Days since shutdown | 0 | 0 | 8 |
| Air rate [m³ (STP)/h] | 4.0 | 3.8 | 4.0 |
| Loading [$g_{o-x}$/m³ (STP)] | 58 | 58 | 58 |
| Salt bath temperature [° C.] | 367 | 370 | 367 |
| o-Xylene [% by wt.] | 0.093 |  | 0.046 |
| Phthalide [% by wt.] | 0.199 |  | 0.107 |

Example 5 (Inventive)

4.0 m³ (STP) of air per hour with loadings of 99 to 99.4% by weight o-xylene of 30 to 100 g/m³ (STP) flowed from the top downward through a tube which corresponds to that described in example 3 and which has also been filled with the same catalyst bed as described in example 3. After a run time of 89 days, at a salt bath temperature of 367° C., an air flow rate of 4 m³ (STP)/h and an o-xylene loading of 58 g/m³ (STP), the supply of the reactant gas to the catalyst was interrupted. The reactor was purged with air for about 2 minutes and then the gas supply was stopped entirely for 12 hours. The catalyst was subsequently started up again at the same salt bath temperature, a reduced o-xylene loading and a reduced air flow rate. Within 5 days, the settings as before the shutdown were attained and the by-products in the product gas composition were analyzed (see Table 5).

TABLE 5

|  | Before the shutdown | Restart | After the shutdown |
|---|---|---|---|
| Days since shutdown | 0 | 0 | 5 |
| Air rate [m³ (STP)/h] | 4.0 | 3.5 | 4.0 |
| Loading [g$_{o-x}$/m³ (STP)] | 92 | 87 | 92 |
| Salt bath temperature [° C.] | 348 | 348 | 348 |
| o-Xylene [% by wt.] | 0.047 |  | 0.037 |
| Phthalide [% by wt.] | 0.071 |  | 0.062 |

Example 6 (Noninventive)

The catalytic oxidation of o-xylene to phthalic anhydride was performed in a salt bath-cooled industrial tubular reactor having an internal tubular diameter of 25 mm. From reactor inlet to reactor outlet, 81 cm of CZ1, 70 cm of CZ2, 85 cm of CZ3, 50 cm of CZ4 and 60 cm of CZ5 were introduced into an iron tube of length 4.0 m with internal width 25 mm. The iron tube was surrounded by a salt melt for temperature regulation.

3.8 m³ (STP) of air per hour with loadings of 98 to 99% by weight o-xylene of 30 to 100 g/m³ (STP) flowed through the tube from the top downward. After a run time of 213 days, the salt bath temperature of 345° C., an air flow rate of 3.8 m³ (STP)/h and an o-xylene loading of 95.4 g/m³ (STP) were kept constant for 9 days and then the by-products in the product gas composition were analyzed (see Table 6).

TABLE 6

| Run time [days] | 213 | 222 |
|---|---|---|
| Air rate [m³ (STP)/h] | 3.8 | 3.8 |
| Loading [g$_{o-x}$/m³ (STP)] | 95.4 | 95.4 |
| Salt bath temperature [° C.] | 345 | 345 |
| o-Xylene [% by wt.] | 0.08 | 0.08 |
| Phthalide [% by wt.] | 0.08 | 0.08 |

Example 7 (Noninventive)

3.8 m³ (STP) of air per hour with loadings of 98 to 99% by weight o-xylene of 30 to 100 g/m³ (STP) flowed from the top downward through a tube which corresponds to that described in example 6 and which has also been filled with the same catalyst bed as described in example 6. After a run time of 273 days, the salt bath temperature of 345° C., an air flow rate of 3.8 m³ (STP)/h and an o-xylene loading of 95.9 g/m³ (STP) were kept constant for 21 days, and the by-products in the product gas composition were analyzed (see Table 7).

TABLE 7

| Run time [days] | 273 | 294 |
|---|---|---|
| Air rate [m³ (STP)/h] | 3.8 | 3.8 |
| Loading [g$_{o-x}$/m³ (STP)] | 95.9 | 95.9 |
| Salt bath temperature [° C.] | 345 | 345 |
| o-Xylene [% by wt.] | 0.06 | 0.06 |
| Phthalide [% by wt.] | 0.06 | 0.07 |

Example 8 (Inventive)

Catalyst Zone 1 (CZ1)
Suspension Mixing and Coating:
2 kg of steatite rings (magnesium silicate) in the form of rings having dimensions of 8 mm×6 mm×5 mm were coated in a fluidized bed apparatus with 855 g of a suspension of 6.9 g of cesium carbonate, 574.6 g of titanium dioxide (Fuji TA 100 C; anatase, BET surface area 20 m²/g), 30.6 g of vanadium pentoxide, 1.75 g of niobium pentoxide, 1588.0 g of demineralized water and 97.1 g of organic binder (copolymer of vinyl acetate and vinyl laurate in the form of a 50% by weight aqueous dispersion).

After calcination of the catalyst at 450° C. for one hour, the active material applied to the steatite rings was 8.9%. The analyzed composition of the active material consisted of 5% $V_2O_5$, 0.2% $Nb_2O_5$, 0.92% Cs, remainder $TiO_2$.

Catalyst Zone 2 (CZ2):
2 kg of steatite rings (magnesium silicate) in the form of rings having dimensions of 8 mm×6 mm×5 mm were coated in a fluidized bed apparatus with 960 g of a suspension of 5.0 g of cesium sulfate, 394.4 g of titanium dioxide (Fuji TA 100 CT; anatase, BET surface area 27 m²/g), 169.5 g of titanium dioxide (Fuji TA 100; anatase, BET surface area 7 m²/g), 43.3 g of vanadium pentoxide, 1.75 g of niobium pentoxide, 0.6 g of potassium sulfate, 0.7 g of ammonium dihydrogenphosphate, 1584.8 g of demineralized water and 109 g of organic binder (copolymer of vinyl acetate and vinyl laurate in the form of a 50% by weight aqueous dispersion).

After calcination of the catalyst at 450° C. for one hour, the active material applied to the steatite rings was 9.0%. The analyzed composition of the active material consisted of 7% $V_2O_5$, 0.2% $Nb_2O_5$, 0.6% Cs, 0.04% K, 0.03% P, remainder $TiO_2$.

Catalyst Zone 3 (CZ3):
2 kg of steatite rings (magnesium silicate) in the form of rings having dimensions of 8 mm×6 mm×5 mm were coated in a fluidized bed apparatus with 950 g of a suspension of 3.5 g of cesium sulfate, 395.6 g of titanium dioxide (Fuji TA 100 CT; anatase, BET surface area 27 m²/g), 169.5 g of titanium dioxide (Fuji TA 100; anatase, BET surface area 7 m²/g), 42.9 g of vanadium pentoxide, 1.75 g of niobium pentoxide, 0.6 g of potassium sulfate, 0.7 g of ammonium dihydrogenphosphate, 1585.6 g of demineralized water and 107.9 g of organic binder (copolymer of vinyl acetate and vinyl laurate in the form of a 50% by weight aqueous dispersion).

After calcination of the catalyst at 450° C. for one hour, the active material applied to the steatite rings was 9.0%. The analyzed composition of the active material consisted of 7% $V_2O_5$, 0.2% $Nb_2O_5$, 0.35% Cs, 0.04% K, 0.03% P, remainder $TiO_2$.

Catalyst Zone 4 (CZ4):
2 kg of steatite rings (magnesium silicate) in the form of rings having dimensions of 8 mm×6 mm×5 mm were coated in a fluidized bed apparatus with 780 g of a suspension of 442.78 g of titanium dioxide (Fuji TA 100 C; anatase, BET surface area 20 m²/g), 111.3 g of vanadium pentoxide, 1.7 g of tungsten trioxide, 3.8 g of ammonium dihydrogenphosphate, 1443.6 g of demineralized water and 88.6 g of organic binder (copolymer of vinyl acetate and vinyl laurate in the form of a 50% by weight aqueous dispersion).

After calcination of the catalyst at 450° C. for one hour, the active material applied to the steatite rings was 8.0%. The analyzed composition of the active material consisted of 20% $V_2O_5$, 0.18% P, 0.24% W, remainder $TiO_2$.

The catalytic oxidation of o-xylene/naphthalene to phthalic anhydride was performed in a salt bath-cooled tubular reactor having an internal tubular diameter of 25 mm. From reactor inlet to reactor outlet, 80 cm of CZ1, 80 cm of CZ2, 90 cm of CZ3 and 70 cm of CZ4 were introduced into an iron tube of length 3.5 m with internal width 25 mm. For temperature regulation, the iron tube was surrounded by a salt melt; a 4 mm external diameter thermowell with installed tensile element served for catalyst temperature measurement.

4.0 m³ (STP) of air per hour with loadings of 99 to 99.4% by weight o-xylene of 0 to 40 g/m³ (STP) and technical naphthalene of 37 to 42 g/m³ (STP) flowed through the tube from the top downward. After a run time of 5 days, at a salt bath temperature of 377° C., an air flow rate of 4 (STP)/h, an o-xylene loading of 10 g/m³ (STP) and a naphthalene loading of 41.2 g/m³ (STP), the supply of the reactant gas to the catalyst was interrupted for 2 hours and replaced by nitrogen. After the 2 hours, the catalyst was charged again with o-xylene- and naphthalene-laden air under conditions identical to those before the shutdown, i.e. a salt bath temperature of 377° C., an air flow rate of 4 m³ (STP)/h, an o-xylene loading of 10 g/m³ (STP) and a naphthalene loading of 41.2 g/m³ (STP). After a further day, the product gas composition was analyzed (see Table 8).

TABLE 8

|  | Before the shutdown | After the shutdown |
| --- | --- | --- |
| Days since shutdown | 0 | 1 |
| Air rate [m³ (STP)/h] | 4.0 | 4.0 |
| Loading [$g_{o-X}$/m³ (STP)] | 10 | 10 |
| Loading [$g_{naphthalene}$/m³ (STP)] | 41.2 | 41.2 |
| Salt bath temperature [° C.] | 377 | 377 |
| o-Xylene [% by wt.] | 0.035 | 0.008 |
| Phthalide [% by wt.] | 0.044 | 0.013 |
| Naphthoquinone [% by wt.] | 2.145 | 1.157 |

It has been found that, under identical conditions, the product quality after the interruption of the supply of the aromatic hydrocarbon to the catalyst has been improved, noticeable by the reduction in the content of phthalide and naphthoquinone, which are underoxidation products, with equal o-xylene and naphthalene concentration in the product.

Example 9 (Inventive)

Catalyst Zone 1 (CZ1)
Suspension Mixing and Coating:

2 kg of steatite rings (magnesium silicate) in the form of rings having dimensions of 8 mm×6 mm×5 mm were coated in a fluidized bed apparatus with 870 g of a suspension of 6.92 g of cesium carbonate, 562.34 g of titanium dioxide (Fuji TA 100 C; anatase, BET surface area 20 m²/g), 42.86 g of vanadium pentoxide, 1.75 g of niobium pentoxide, 1587.96 g of demineralized water and 98.8 g of organic binder (copolymer of vinyl acetate and vinyl laurate in the form of a 50% by weight aqueous dispersion).

After calcination of the catalyst at 450° C. for one hour, the active material applied to the steatite rings was 8.9%. The analyzed composition of the active material consisted of 4.62% $V_2O_5$, 0.28% $Nb_2O_5$, 0.99% Cs, remainder $TiO_2$.

Catalyst Zone 2 (CZ2):

2 kg of steatite rings (magnesium silicate) in the form of rings having dimensions of 8 mm×6 mm×5 mm were coated in a fluidized bed apparatus with 970 g of a suspension of 5.3 g of cesium sulfate, 562.3 g of titanium dioxide (Fuji TA 100 C; anatase, BET surface area 20 m²/g), 39.0 g of vanadium pentoxide, 1.75 g of niobium pentoxide, 1441.6 g of demineralized water and 110.2 g of organic binder (copolymer of vinyl acetate and vinyl laurate in the form of a 50% by weight aqueous dispersion).

After calcination of the catalyst at 450° C. for one hour, the active material applied to the steatite rings was 9.0%. The analyzed composition of the active material consisted of 7% $V_2O_5$, 0.2% $Nb_2O_5$, 0.67% Cs, remainder $TiO_2$.

Catalyst Zone 3 (CZ3):

2 kg of steatite rings (magnesium silicate) in the form of rings having dimensions of 8 mm×6 mm×5 mm were coated in a fluidized bed apparatus with 900 g of a suspension of 3.5 g of cesium sulfate, 565.5 g of titanium dioxide (Fuji TA 100 C; anatase, BET surface area 20 m²/g), 42.9 g of vanadium pentoxide, 1.75 g of niobium pentoxide, 1441.6 g of demineralized water and 102.2 g of organic binder (copolymer of vinyl acetate and vinyl laurate in the form of a 50% by weight aqueous dispersion).

After calcination of the catalyst at 450° C. for one hour, the active material applied to the steatite rings was 9.0%. The analyzed composition of the active material consisted of 7% $V_2O_5$, 0.2% $Nb_2O_5$, 0.4% Cs, remainder $TiO_2$.

Catalyst Zone 4 (CZ4):

2 kg of steatite rings (magnesium silicate) in the form of rings having dimensions of 8 mm×6 mm×5 mm were coated in a fluidized bed apparatus with 865 g of a suspension of 198.3 g of titanium dioxide (Fuji TA 100 CT; anatase, BET surface area 20 m²/g), 368.3 g of titanium dioxide (Fuji TA 100; anatase, BET surface area 7 m²/g), 42.9 g of vanadium pentoxide, 1.75 g of niobium pentoxide, 5.1 g of ammonium dihydrogenphosphate, 1587.9 g of demineralized water and 98.3 g of organic binder (copolymer of vinyl acetate and vinyl laurate in the form of a 50% by weight aqueous dispersion).

After calcination of the catalyst at 450° C. for one hour, the active material applied to the steatite rings was 9.6%. The analyzed composition of the active material consisted of 7% $V_2O_5$, 0.2% $Nb_2O_5$, 0.22% P (introduced into the suspension as dihydrogenphosphate), remainder $TiO_2$.

The catalytic oxidation of o-xylene/naphthalene to phthalic anhydride was performed in a salt bath-cooled tubular reactor having an internal tubular diameter of 25 mm. From reactor inlet to reactor outlet, 80 cm of CZ1, 80 cm of CZ2, 90 cm of CZ3 and 90 cm of CZ4 were introduced into an iron tube of length 3.5 m with internal width 25 mm. For temperature regulation, the iron tube was surrounded by a salt melt; a 4 mm external diameter thermowell with installed tensile element served for catalyst temperature measurement.

The tube was passed from the top downward with 4.0 m³ (STP) of air per hour with loadings of 99 to 99.4% by weight o-xylene of 0 to 25 g/m³ (STP) and technical naphthalene of 38 to 41 g/m³ (STP). After a run time of 4 days, at a salt bath temperature of 380° C., an air flow rate of 4 m³ (STP)/h, an o-xylene loading of 0 g/m³ (STP) and a naphthalene loading of 40 g/m³ (STP), the supply of the reactant gas to the catalyst was interrupted for 4 hours and replaced by nitrogen. After the 4 hours, the catalyst was charged again with naphthalene-laden air under conditions identical to those before the shutdown, i.e. a salt bath temperature of 380° C., an air flow rate of 4 m³ (STP)/h, an o-xylene loading of 0 g/m³ (STP) and a naphthalene loading of 40 g/m³ (STP). After a further day, the product gas composition was analyzed (see Table 9).

TABLE 9

|  | Before the shutdown | After the shutdown |
| --- | --- | --- |
| Days since shutdown | 0 | 1 |
| Air rate [m³ (STP)/h] | 4.0 | 4.0 |
| Loading [$g_{o-x}$/m³ (STP)] | 0 | 0 |
| Loading [$g_{naphthalene}$/m³ (STP)] | 40 | 40 |
| Salt bath temperature [° C.] | 380 | 380 |
| o-Xylene [% by wt.] | 0 | 0 |
| Phthalide [% by wt.] | 0 | 0 |
| Naphthoquinone [% by wt.] | 1.267 | 0.516 |

It has been found that, under identical conditions, the product quality after the interruption of the supply of the aromatic hydrocarbon to the catalyst has been improved, noticeable by the reduction in the content of naphthoquinone, an underoxidation product, with equal naphthalene concentration in the product.

The invention claimed is:

1. A process for preparing phthalic anhydride by gas phase oxidation of o-xylene and/or napthalene, the process comprising:
    continuously passing a gas stream comprising at least one aromatic hydrocarbon selected from the group consisting of o-xylenes and naphthalene, and molecular oxygen over a thermostatted catalyst in at least one reactor tube, wherein said at least one reactor tube is surrounded by a heat carrier medium,
    interrupting the supply of the at least one aromatic hydrocarbon to the catalyst for a period after putting the catalyst on stream and resuming the supply of the at least one aromatic hydrocarbon to the catalyst at the end of the period;
    wherein the temperature of the heat carrier medium is set to a higher value at the end of the period than before the interruption of the supply of the aromatic hydrocarbon to the catalyst.

2. The process according to claim 1, wherein the length of the period is in the range of 30 minutes to 200 days.

3. The process according to claim 1, wherein a hydrocarbon-free gas stream is passed over the catalyst during the period.

4. The process according to claim 3, wherein the hydrocarbon-free gas stream passed over the catalyst comprises between 0 and 50% by volume of oxygen and otherwise comprises air, nitrogen and/or noble gases.

5. The process according to claim 1, wherein no gas stream is passed over the catalyst during the period.

6. The process according to claim 1, wherein the gas flow rate is set to a lower value at the end of the period than before the interruption of the supply of the aromatic hydrocarbon to the catalyst.

7. The process according to claim 1, wherein the loading of the gas stream with aromatic hydrocarbon is set to a lower value at the end of the period than before the interruption of the supply of the aromatic hydrocarbon to the catalyst.

8. The process according to claim 1, wherein the temperature of the heat carrier medium is set to a 1 to 5° C. higher value at the end of the period than before the interruption of the supply of the aromatic hydrocarbon to the catalyst.

9. The process according to claim 1, wherein the gas flow rate is set to a 5 to 15% lower value at the end of the period than before the interruption of the supply of the aromatic hydrocarbon to the catalyst.

10. The process according to claim 1, wherein the loading of the gas stream with aromatic hydrocarbon is set to a 5 to 30% lower value at the end of the period than before the interruption of the supply of the aromatic hydrocarbon to the catalyst.

11. The process according to claim 1, wherein the interrupting occurs by replacing the reactant gas with nitrogen for two hours to 52 days.

12. The process according to claim 1, wherein the interrupting occurs by purging with air for 2 minutes, then stopping the flow of gas for 12 hours to three days.

13. A process for preparing phthalic anhydride by gas phase oxidation of o-xylene and/or napthalene, the process comprising:
    continuously passing a gas stream comprising at least one aromatic hydrocarbon selected from the group consisting of o-xylenes and naphthalene, and molecular oxygen over a thermostatted catalyst in at least one reactor tube, wherein said at least one reactor tube is surrounded by a heat carrier medium,
    interrupting the supply of the at least one aromatic hydrocarbon to the catalyst for a period after putting the catalyst on stream and resuming the supply of the at least one aromatic hydrocarbon to the catalyst at the end of the period;
    wherein the temperature of the heat carrier medium is set to a 1 to 5° C. higher value at the end of the period than before the interruption of the supply of the aromatic hydrocarbon to the catalyst;
    wherein the gas flow rate is set to a 5 to 15% lower value at the end of the period than before the interruption of the supply of the aromatic hydrocarbon to the catalyst; and
    wherein the interrupting occurs by purging with air for 2 minutes, then stopping the flow of gas for 12 hours to three days.

* * * * *